United States Patent
Ecker et al.

(10) Patent No.: US 9,693,716 B2
(45) Date of Patent: Jul. 4, 2017

(54) OPTICAL SENSOR SYSTEM AND MEASUREMENT METHOD

(75) Inventors: Robert Michael Ecker, Lino Lakes, MN (US); Timothy J. Davis, Coon Rapids, MN (US); James D. Reinke, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 1018 days.

(21) Appl. No.: 13/044,119

(22) Filed: Mar. 9, 2011

(65) Prior Publication Data
US 2012/0232354 A1   Sep. 13, 2012

(51) Int. Cl.
  A61B 5/1455  (2006.01)
  A61B 5/046   (2006.01)
  G01D 5/34    (2006.01)
  G01D 18/00   (2006.01)

(52) U.S. Cl.
  CPC .......... *A61B 5/14551* (2013.01); *A61B 5/046* (2013.01); *A61B 5/14552* (2013.01); *G01D 5/34* (2013.01); *G01D 18/008* (2013.01)

(58) Field of Classification Search
  CPC .............. A61B 5/1455; A61B 5/14551; A61B 5/14532; A61B 5/14552; A61B 5/0059; H04N 5/235; H04N 5/2355
  USPC ....... 600/310, 322, 323, 330, 331, 336, 341, 600/473, 476; 356/41
  See application file for complete search history.

(56) References Cited

U.S. PATENT DOCUMENTS

| | | | |
|---|---|---|---|
| 3,847,483 A | 11/1974 | Shaw | |
| 4,791,935 A | 12/1988 | Baudino | |
| 5,820,550 A | 10/1998 | Polson | |
| 6,125,290 A * | 9/2000 | Miesel | .......... 600/325 |
| 6,198,952 B1 | 3/2001 | Miesel | |
| 6,397,092 B1 | 5/2002 | Norris | |
| 6,564,077 B2 | 5/2003 | Mortara | |
| 6,879,850 B2 | 4/2005 | Kimball | |
| 6,944,488 B2 | 9/2005 | Roberts | |
| 7,164,938 B2 | 1/2007 | Geddes | |
| 7,471,970 B2 | 12/2008 | Zhang | |
| 7,512,431 B2 | 3/2009 | Roberts | |
| 2006/0092328 A1 | 5/2006 | Anderson | |
| 2006/0132619 A1* | 6/2006 | Choi et al. | ................. 348/224.1 |
| 2008/0306390 A1 | 12/2008 | Cinbas | |
| 2009/0259116 A1* | 10/2009 | Wasserman et al. | ......... 600/323 |

FOREIGN PATENT DOCUMENTS

EP    341059 A2    11/1989

* cited by examiner

*Primary Examiner* — Eric Winakur
*Assistant Examiner* — Chu Chuan (JJ) Liu

(57) ABSTRACT

A medical device including an optical sensor is configured to measure an optical signal by integrating a current induced on a light detector of the optical sensor to obtain a voltage signal. The voltage signal is compared to a threshold. Responsive to the voltage signal reaching the threshold, an optical sensor control parameter is adjusted. The optical sensor is operated to produce the voltage signal using the adjusted control parameter.

24 Claims, 6 Drawing Sheets

OPTICAL SENSOR SYSTEM AND MEASUREMENT METHOD

TECHNICAL FIELD

The disclosure relates generally to implantable medical devices and, in particular, to an implantable optical sensor and associated method combining amplitude and time-based measurements for measuring an optical signal.

BACKGROUND

Implantable optical sensors have been used for monitoring relative changes in a patient's blood oxygen saturation. Acute or chronic ambulatory monitoring of a patient's blood oxygen saturation has many clinically useful applications, among which are monitoring a patient condition relating to his or her hemodynamic status, cardiac function, tissue perfusion, or respiration function. An implantable optical sensor employs at least one light source, e.g. a light emitting diode (LED), and at least one light detector, e.g. a photodiode. The light source emits light from the sensor which is reflected or transmitted through an adjacent body tissue back to the sensor. The light detector, also referred to herein as a "photodetector", is a light sensitive device that generates a current signal proportional to the intensity of light received by the light detector. The attenuation of light emitted by the sensor, as measured by the light detector, allows a characteristic of the blood or tissue to be monitored based on changes in light attenuation by the blood or tissue over time.

DETAILED DESCRIPTION

Figure 1:
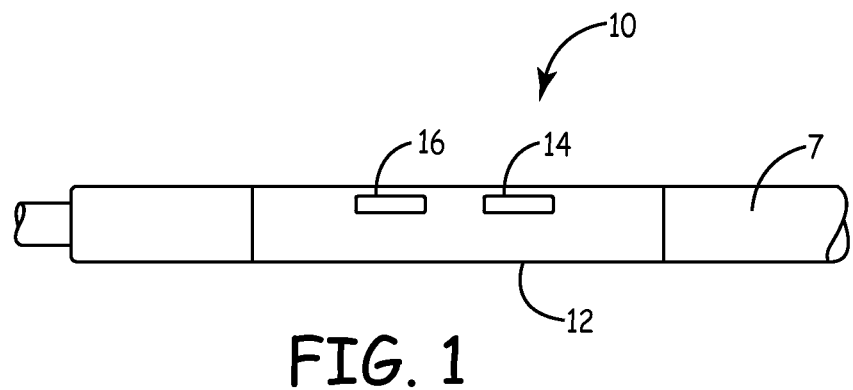
FIG. 1 is an enlarged view of an optical sensor.

In the following description, references are made to illustrative embodiments. It is understood that other embodiments may be utilized without departing from the scope of the disclosure. For purposes of clarity, identical reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

At least two approaches have been taken to develop optical sensor systems which measure optical signals correlated to blood oxygen saturation. One is a time-based system in which a time interval required for the light detector current to charge a capacitor to a predefined voltage level is measured. The time interval measurement is inversely proportional to the intensity of the remitted light and the resulting light detector current. The other approach is an amplitude-based measurement. At the end of a predefined time interval, the voltage amplitude to which a capacitor is charged by the light detector current is measured.

Both of these approaches rely on the formula $i=C*dV/dt$. The value i is the light detector current which varies with the intensity of the remitted light, i.e. the light received by the sensor. C is the capacitance of an integration capacitor included in the optical sensor circuitry. In the first, time-based approach, the change in time (dt) is measured for a defined change in voltage stored by the capacitor. In the second, amplitude-based approach, the change in voltage (dV) stored by the capacitor is measured for a defined change in time, dt.

Each approach has advantages and limitations when implemented in a medical device including an optical sensor used for monitoring a patient. For example, in a time-based measurement system, if the remitted light intensity is low, the time interval required to reach the predefined voltage change will become long. The sampling rate of the time interval measurements can therefore become slow or unpredictable. In an amplitude-based system, high signal intensity can result in signal clipping if the voltage change reaches a maximum range before the end of the predefined time interval. A need remains for an optical sensor signal measurement system that utilizes the advantages and overcomes the limitations associated with each approach.

FIG. 1 is an enlarged view of an optical sensor 10 that may be used in practicing the methods described herein. Optical sensor 10 is shown implemented in an elongated medical lead that is adapted to be coupled to an implantable medical device (IMD) such as a pacemaker, implantable cardioverter defibrillator (ICD), hemodynamic monitor, drug delivery pump, neurostimulator or other device capable of monitoring physiological signals in a patient. An IMD coupled to optical sensor 10 may or may not be configured to deliver a therapy. When therapy delivery capabilities are present, the IMD may be configured to control the therapy delivery, all or in part, in response to a signal from the optical sensor 10.

A sensor housing 12 is provided for enclosing electronic optical sensor components. Lenses 14 and 16 are respectively provided for passing light emitted from a light emitting portion of sensor 10 and passing reflected light to a light detecting portion of sensor 10, both of which reside within housing 12. A single lens may be used in lieu of two lenses 14 and 16 as shown here.

Lead body 7 is provided for carrying insulated conductors from the circuitry included in sensor 10 to a proximal lead connector assembly (not shown) located at a proximal end of the medical lead used for mechanically and electrically connecting the lead to an IMD. A lead carrying optical sensor 10 may additionally include other types of sensors and/or electrodes according to the intended use of the lead.

In alternative embodiments, sensor 10 may be incorporated in or along a housing or lead connector block of an IMD such as a pacemaker, ICD, hemodynamic monitor, drug delivery device, neurostimulator or other patient monitoring or therapy delivery device instead of being carried by a medical electrical lead or catheter. In still other embodiments, sensor 10 may be implemented in a wireless sensor deployable in any body location without being tethered to a medical lead or catheter. A wireless optical sensor includes a communication module for wirelessly transmitting sensor signals to another IMD or an external device and includes a power supply and circuitry necessary for operating the optical sensor.

Figure 2:
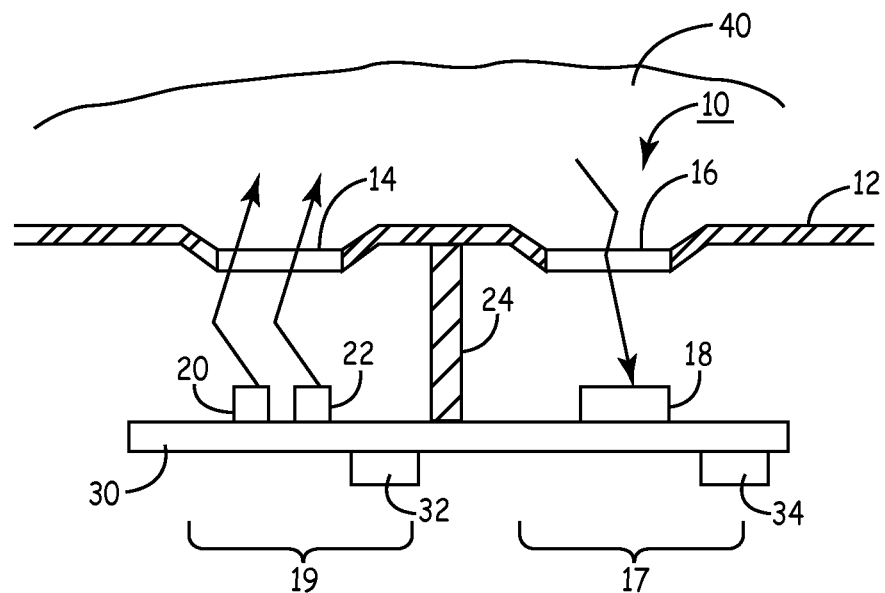
FIG. 2 is a sectional view of the optical sensor of FIG. 1.

FIG. 2 is a sectional view of optical sensor 10 of FIG. 1. Sensor 10 is shown to include two light sources 20 and 22 mounted within a housing 12 of sensor 10. Two-wavelength optical sensing systems are often used in the field of blood oximetry. In a two-wavelength system, the reflected light signal of one wavelength that changes in intensity with blood oxygen saturation is normalized by a second wavelength of light which is less dependent on blood oxygen saturation but dependent on other physiological changes in the measured blood volume, such as blood flow velocity and hematocrit concentration. For example, one light source 20 may be an LED emitting red light and the second light source 22 may be an LED emitting infrared light.

Methods are described herein for combining time-based and amplitude-based measurements in an optical signal. These methods and associated apparatus may be used in conjunction with any optical sensor regardless of the number or light spectrum of the light sources included in an emitting portion of the optical sensor. For example, a light source included in optical sensor 10 may be a single light source emitting white light. Alternatively, one or more light sources emitting a selected light wavelength or narrowband spectrum of wavelengths may be included in emitting portion 19. The emitted light generally includes desired wavelength(s) at which light attenuation by the adjacent body tissue or fluid 40 is to be measured.

Illustrative embodiments described herein relate primarily to an optical sensor used in blood oximetry applications. The methods described, however, may be practiced in conjunction with any optical sensing application, and are not limited to particular wavelengths of emitted and measured light. In other applications, other light wavelengths or combinations of wavelengths may be measured to determine attenuation of light corresponding to a chromophore or metabolite of interest in a targeted body tissue or fluid for monitoring a patient condition. Any number of light sources may therefore be included in a light emitting portion 19 of sensor 10.

Light sources 20 and 22 are mounted on one side of a sensor hybrid circuit board 30 in a light emitting portion 19 of sensor 10. Light sources are electrically coupled to integrated circuitry 32 for delivering appropriately-timed drive signals to sources 20 and 22 for controlling the intensity, frequency and time intervals of emitted light. When more than one light source is included in emitting portion 19, light may be emitted sequentially in a time-multiplexed manner or simultaneously in a frequency multiplexed manner.

Emitted light passes through lens 14 into an adjacent tissue volume 40, which may be a blood-perfused or non-perfused body tissue, a blood volume or other body fluid volume. As used herein, the term "tissue" includes body fluids such as blood. As such, volume 40 may be a volume of blood flowing through a blood vessel or a heart chamber. In other applications, volume 40 is a body tissue, such as muscle tissue, brain tissue, cardiac tissue, etc. being monitored by the optical sensor 10.

Light that is reflected or scattered by the tissue volume 40 is received by sensor 10 through lens 16 of light detecting portion 17. Sensor 10 is shown in a "reflection" configuration in that the emitting and detecting portions 19 and 17 are arranged in a side-by-side manner, along a common side of tissue volume 40, such that remitted light is reflected or scattered by tissue volume 40 back into light detecting portion 17. In an alternative embodiment, sensor 10 may be configured in a "transmission" configuration wherein the emitting and detecting portions 19 and 17 are arranged in facing opposition. The emitting and detecting portions 19 and 17 would be positioned on approximately opposite sides of the tissue volume 40 with tissue volume 40 positioned between the opposing emitting and detecting portions. In a transmission configuration, remitted light is light that is transmitted through the tissue volume 40.

A light detector 18 is mounted on hybrid circuit board 30, or alternatively a separate circuit board, in a light detecting portion 17 of sensor 10. Detector 18 is electrically coupled to integrated circuitry 34 for receiving current emitted by detector 18 and for transferring an analog or digital signal to signal processing circuitry included in the IMD. In various embodiments, one or more light detecting elements may be included in light detecting portion 17, which may be sensitive to a wide or narrow-band spectrum of light wavelengths according to the particular monitoring application.

Integrated circuits 32 and 34 are electrically coupled to conductors (not shown), which may extend through a medical lead body as described above in conjunction with FIG. 1 to circuitry included in an IMD. In an alternative embodiment, sensor 10 is not carried along a lead and is incorporated in the housing of an IMD in which case integrated circuits 32 and 34 are electrically coupled to other IMD circuits by conductors or wires within the IMD housing.

Sensor 10 includes light barrier or baffle 24 disposed between light emitting portion 19 and light detecting portion 17. Light barrier 24 prevents the direct, reflected or refracted transmission of emitted light that is not scattered by tissue volume 40 into light detecting portion 17 for spurious detection by light detector 18. Lenses 14 and 16 are typically formed of a flat panel, cylinder or half-cylinder of glass, sapphire, ruby, quartz or any other suitable light transparent material. Light emitting portion 19 and light detecting portion 17 may each have a discrete lens 14 and 16, respectively. Alternatively, a single lens may be provided with light barrier 24 separating the light detecting and emitting portions 17 and 19, respectively.

In a two-wavelength optical sensor such as sensor 10 shown in FIG. 2, the amount of remitted light corresponding to one wavelength, e.g. red, is normalized by the amount of remitted light corresponding to a second wavelength, e.g. infrared, to estimate the concentration of a metabolite, e.g. oxygen, present in the measurement volume adjacent the sensor. In an oxygen sensor, red light and infrared light is emitted by the emitting portion 19 and scattered by the adjacent tissue volume 40. A portion of the emitted red and infrared light returns to the sensor 10 and is detected by the detecting portion 17. Red light is dependent on oxygen saturation of hemoglobin present in a measurement volume of the sensor. Infrared light is somewhat less dependent on oxygen saturation than red light and in an inverse relation compared to red light. A photodetector current is measured for each light wavelength and the red light measurement is normalized by the infrared light measurement to account for differences in hematocrit, blood flow velocity and other common-mode signals. This ratio of measured red and infrared light may be used to estimate a measurement of oxygen saturation present in blood in the adjacent tissue volume 40 and compare relative changes in oxygen saturation over time.

Accurate estimation of oxygen saturation, or changes in oxygen saturation, relies on accurate measurement of the remitted light intensity. As discussed above, two approaches for measuring remitted light are the time-based and the amplitude-based methods. For example, using the time-based method to measure oxygen saturation, the time required for the current induced on photodetector 18, integrated over a capacitor, to reach a predetermined voltage amplitude is measured. A red light and an infrared light time interval measurement is obtained by sequential activation of light sources 20 and 22 embodied as red and infrared LEDs. The time interval measured for the red light signal to reach a predetermined voltage amplitude is normalized by the time interval measured for the infrared light signal to reach the predetermined voltage amplitude.

One advantage of a time-based method is that the voltage signal never clips because the voltage amplitude is set at a predetermined value and the time interval to reach that predetermined voltage is measured. A limitation of the time-based method is that when the light signal is high, measured time intervals can be very short requiring a high speed clock, which requires high power that is somewhat wasted when time intervals are relatively longer. On the other hand, if a very low signal current is being measured, for example when measuring ambient light for use in correcting remitted light measurements for the presence of ambient light, time intervals can become very long, approaching infinity as ambient light approaches zero. A low light signal resulting in long measured time intervals will use significant power if the light source(s) need to be emitting light for the long time intervals.

In the amplitude-based method for oxygen saturation monitoring, capacitor voltage amplitude is measured at the end of a predetermined time interval for both red and infrared light to obtain a ratio or red to infrared light for estimating oxygen saturation. One advantage of the amplitude-based method is that the known time interval allows the system to operate in a time-efficient, consistent and predictable manner. Using fixed-length time intervals provides a regular sampling rate and enables high sampling rates to be used when a relatively short time interval is chosen, which conserves battery capacity. High or over-sampled light intensity measurements can be averaged for improved signal-to-noise ratio. Since the light sources are activated for a controlled time interval, which can be kept relatively short, heating in the vicinity of the optical sensor can be minimized. Ambient light measurements over short time-intervals can be interspersed with the remitted light measurements, allowing correction or detection of potential measurement error due to ambient light fluctuations.

A limitation of the amplitude-based method, however, is that when the light intensity is high the voltage signal can clip at the maximum input range of the A/D converter. A clipped signal prevents accurate estimation of the oxygen saturation, or of any other chromophore being measured. A portion of the A/D converter is generally reserved for fluctuations in ambient light and motion artifact. A higher than expected photodetector current due to ambient light, motion, or increased remitted light signal intensity, however, may cause the optical sensor signal to clip.

Figure 3A:
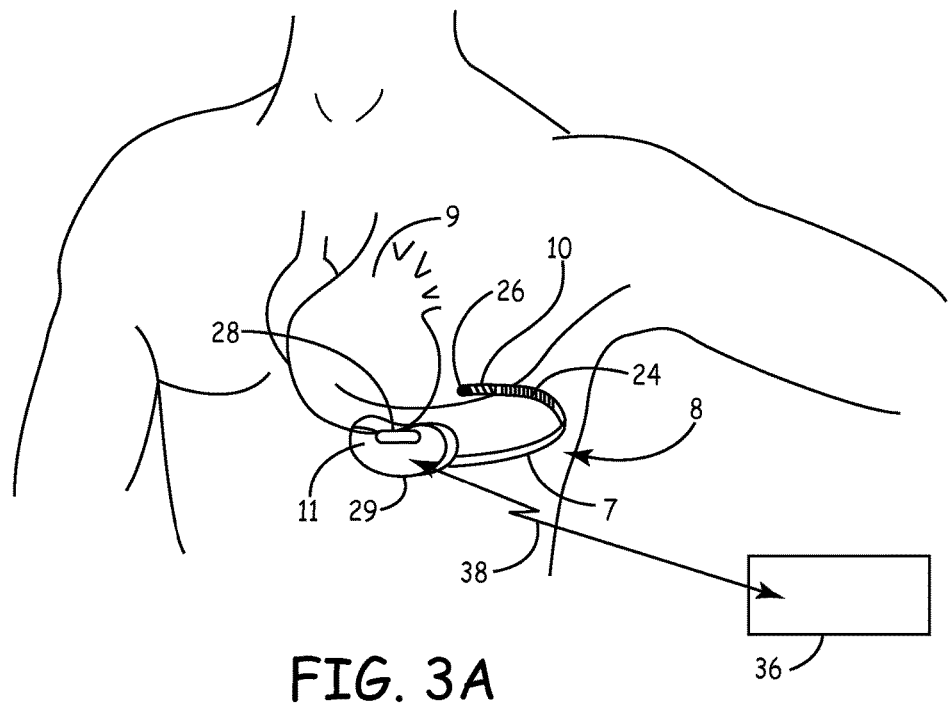
FIG. 3A is a schematic diagram of an implantable medical device (IMD) system including an optical sensor according to one embodiment.

FIG. 3A is a schematic diagram of an implantable medical device (IMD) system including a subcutaneous IMD 11 coupled to lead 8 according to one embodiment for monitoring blood oxygen saturation. IMD 11 is embodied as a subcutaneous cardioverter defibrillator which may be implanted outside the ribcage of the patient in operative relation to the heart 9 for sensing subcutaneous ECG signals. A subcutaneous sensing and cardioversion/defibrillation therapy delivery lead 8 in electrical communication with IMD 11 is tunneled subcutaneously into a posterior location, e.g. adjacent a portion of a latissimus dorsi muscle of the patient. Lead 8 is tunneled from the median implant pocket of IMD 11 laterally and posteriorly to a location opposite the heart such that the heart 9 is disposed between the IMD 11 and the distal electrode coil 24 and distal sensing electrode 26 of lead 8 for sensing ECG signals and delivering defibrillation shocks to the patient.

In this illustrative embodiment, IMD 11 and/or lead 8 may be configured to carry an optical sensor for monitoring blood oxygen saturation. Lead 8 is shown to include optical sensor 10 near a distal end of lead 8. Alternatively or additionally, IMD 11 may include an optical sensor 28 incorporated along the housing 29 of the IMD. The optical sensor 10 or 28 may be used for monitoring blood oxygen saturation for use in detecting or confirming cardiac fibrillation and/or for use in confirming the success of a delivered defibrillation shock. While FIG. 3A illustrates one particular implementation and use of an implantable optical sensor, it is recognized that numerous applications and associated systems and implant configurations may utilize an optical sensor and may incorporate the methods described herein for monitoring an optical signal.

Further referring to FIG. 3A, an external programmer 36 is shown in telemetric communication with IMD 11 by a telemetric communication link 38. Communication link 38 may be any appropriate radiofrequency link such as Bluetooth, WiFi, MICS or the like. Programmer 36 provides a user interface for programming IMD 11 and retrieving data acquired by IMD 11. With respect to the monitoring methods employing an optical sensor described herein, programmer 36 may be used to program optical sensor control parameters including an integration time interval, an integration capacitance, light source drive current(s), the frequency that the optical sensor signal is monitored, the time interval over which optical sensor signal monitoring is performed, and the frequency of automatically adjusting optical sensor control parameters. Methods for automatically adjusting sensor control parameters will be further described herein.

Figure 3B:
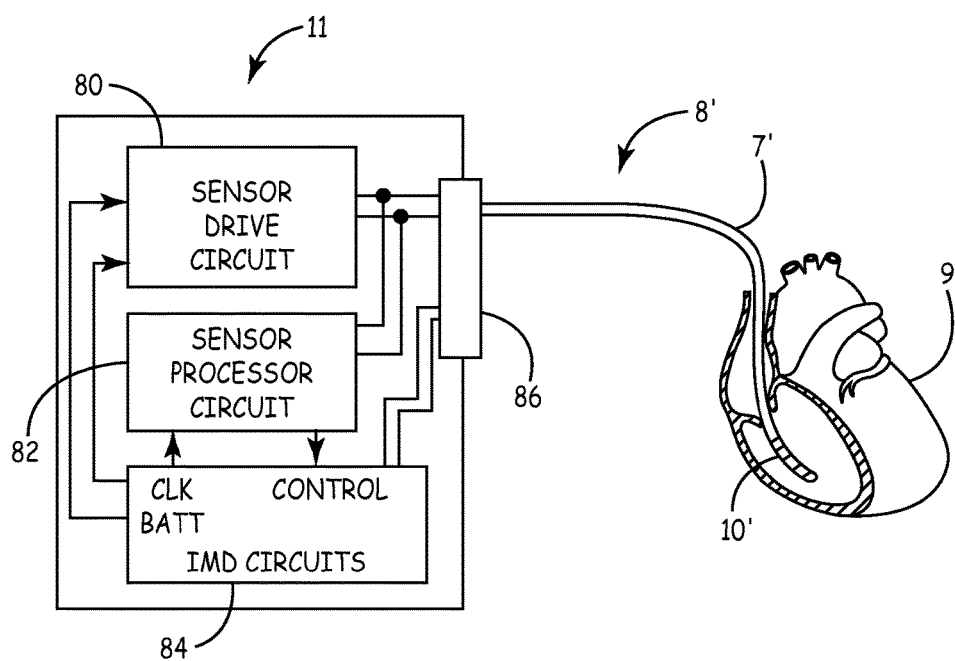
FIG. 3B is a functional block diagram of an IMD system including an optical sensor according to an alternative embodiment.

FIG. 3B is a functional block diagram of IMD 11. In FIG. 3B, IMD 11 is shown coupled to a transvenous medical electrical lead 8' carrying an optical sensor 10' according to an alternative IMD system configuration including an optical sensor. In this case, optical sensor 10' is positioned in the right ventricle of the patient's heart 9. Optical sensor 10' carried by a transvenous lead 7', however, may be deployed to other locations in the patient's cardiovascular system, including venous and intracardiac locations. Optical sensor 10' is typically mechanically and electrically coupled to the distal ends of lead conductors disposed within the elongated body 7' of lead 8'. Optical sensor 10', however, may be positioned at other more proximal locations along lead 8'. A proximal lead connector (not shown) is coupled to the proximal ends of insulated lead conductors and provides electrical connection of sensor 10' to sensor drive circuit 80 and sensor processor circuit 82 via an IMD connector block 86.

When IMD 11 includes cardiac pacing capabilities, lead 8' may additionally include pacing, sensing and/or defibrillation electrodes generally disposed at the distal end of lead 8' in operative relation to one or more heart chambers. Alternatively, additional pacing and sensing leads are included in the IMD system. Cardiac pacing and sensing control circuitry, a clock, and a battery for powering IMD operations are included in IMD circuitry 84. Circuitry included in an implantable medical device and its operation with an optical sensor is generally described, for example, in U.S. Pat. No. 6,125,290 (Miesel et al.), U.S. Pat. No. 4,791,935 (Baudino et al.), and U.S. Pat. Publication No. 2008/0306390 (Cinbis), all of which are hereby incorporated herein by reference in their entirety.

The functionality of IMD 11 described generally with regard to optical sensor 10 or 10' may apply generally to any optical sensor configuration, including subcutaneous lead-based sensor 10, subcutaneous sensor 28 incorporated along the housing 29 of IMD 11, or a transvenous lead-based sensor 10'. Sensor drive circuit 80 provides the operational power for the optical sensor and controls the timing of optical sensor operation. Sensor processor circuit 82 receives optical sensor signal output and processes the signal output to estimate a chromophore measurement corresponding to measured light intensity.

Sensor drive circuit 80 controls the current applied to the light sources included in the emitting portion of the optical sensor. The drive current used to activate the light source(s) can be increased or decreased to control the intensity of emitted light during sensor operation. Sensor drive circuit 80 further controls the time intervals that the light sources are activated. In one embodiment, the sensor drive circuit activates the light source(s) for a predetermined integration time interval during amplitude-based light measurements. An activation or emission time corresponding to an integration time interval used during amplitude-based measurements and the light source drive current may be programmable parameters.

Sensor processor circuit 82 may include an A/D converter, filter, and other circuitry used for processing the sensor output signal for determining measurements of remitted light intensity and estimating a measurement of a chromophore present in the adjacent tissue volume. Sensor processor circuit 82 may be configured to control the capacitance over which the photodetector current signal is integrated and may control the integration time interval.

IMD circuitry 84 provides a battery power source and clock signal for sensor drive circuit 80 and sensor processor circuit 82. IMD circuit 84 receives the sensor processor output signal for use in detecting a physiological condition of the patient, which may be used in controlling a therapy delivered by IMD 11. IMD circuit 84 controls sensor drive circuit 80 to operate sensor 10 (or 10' or 28) as needed according to a programmed patient monitoring schedule or on a triggered basis to detect patient conditions or manage a device delivered therapy.

Figure 4:
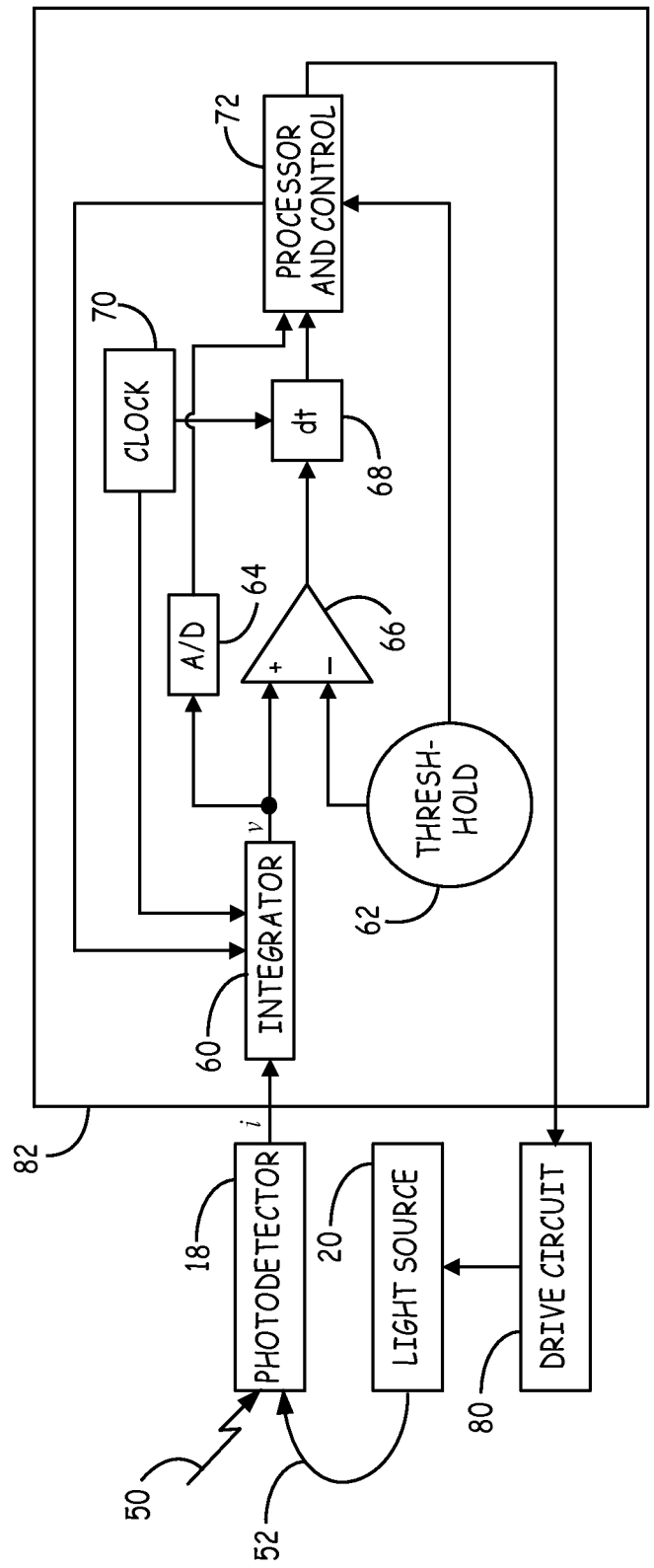
FIG. 4 is a functional block diagram of optical sensor signal processing circuitry which may be included in an optical sensor according to one embodiment.

FIG. 4 is a functional block diagram of optical sensor signal processing circuitry which may be included in processor circuit 82. The functionality shown in FIG. 4 may be implemented within an optical sensor housing 12, e.g. in hybrid circuits 32 and 34 (FIG. 1), within the housing 12 of an IMD coupled to an optical sensor either wirelessly or hard-wired for receiving a photodetector signal, or a combination of both.

A current induced on photodetector 18 is provided as input to an integrator 60. The current signal is induced in response to remitted light that may be a combination of ambient light 50 incident on the light detecting portion of the optical sensor and light 52 emitted by light source 20 and reflected or transmitted to photodetector 18. Drive circuit 80 provides an activation signal for causing light source 20 to emit light according to a monitoring protocol.

Integrator 60 integrates the current signal over a programmable capacitance and programmable integration time interval provided by clock 70. The voltage signal at the end of the integration time interval is provided to A/D converter 64 which in turn provides sampled voltage measurements to processor and control 72. Processor and control 72 uses the sampled voltage signal to compute a measurement of a chromophore in an adjacent tissue volume for use in monitoring a patient condition and/or controlling a therapy delivered by an IMD.

As will be further described below, the integrator voltage signal is provided as input to a comparator 66 during the integration time interval for comparison to a threshold 62. The threshold 62 is set at a level below a maximum input range of A/D converter 64. If the voltage signal reaches this pre-clip threshold before expiration of the integration time interval, a comparator output signal causes the time interval (dt) at which the pre-clip threshold was reached to be measured at timer block 68. This time interval measurement is provided as input to processor and control 72 for use in adjusting optical sensor control parameters. It is understood that the time interval dt may be measured upon expiration of a clock interval and is thus limited in resolution by the clock resolution. The time interval measured will correspond to a voltage that is at or greater than the pre-clip threshold at the expiration of a given time interval.

Processor and control 72 adjusts an optical sensor control parameter in response to the pre-clip threshold being reached to set an estimated integrator voltage signal output at the expiration of an integration time interval to be within the A/D converter input range. In other words, in response to the pre-clip threshold being reached, the sensor control parameters are automatically adjusted to adjust the sensor output signal back within the range of the A/D converter. By making this adjustment, clipping of the integrator voltage signal can be avoided or minimized.

The processor and control 72 may automatically adjust the current drive signal provided by drive circuit 80 and applied to the emitting portion light source(s). Additionally or alternatively, an integration time interval or an integration capacitance used by integrator 60, over which the current signal is integrated, is adjusted in response to a pre-clip threshold being reached.

Figure 5:
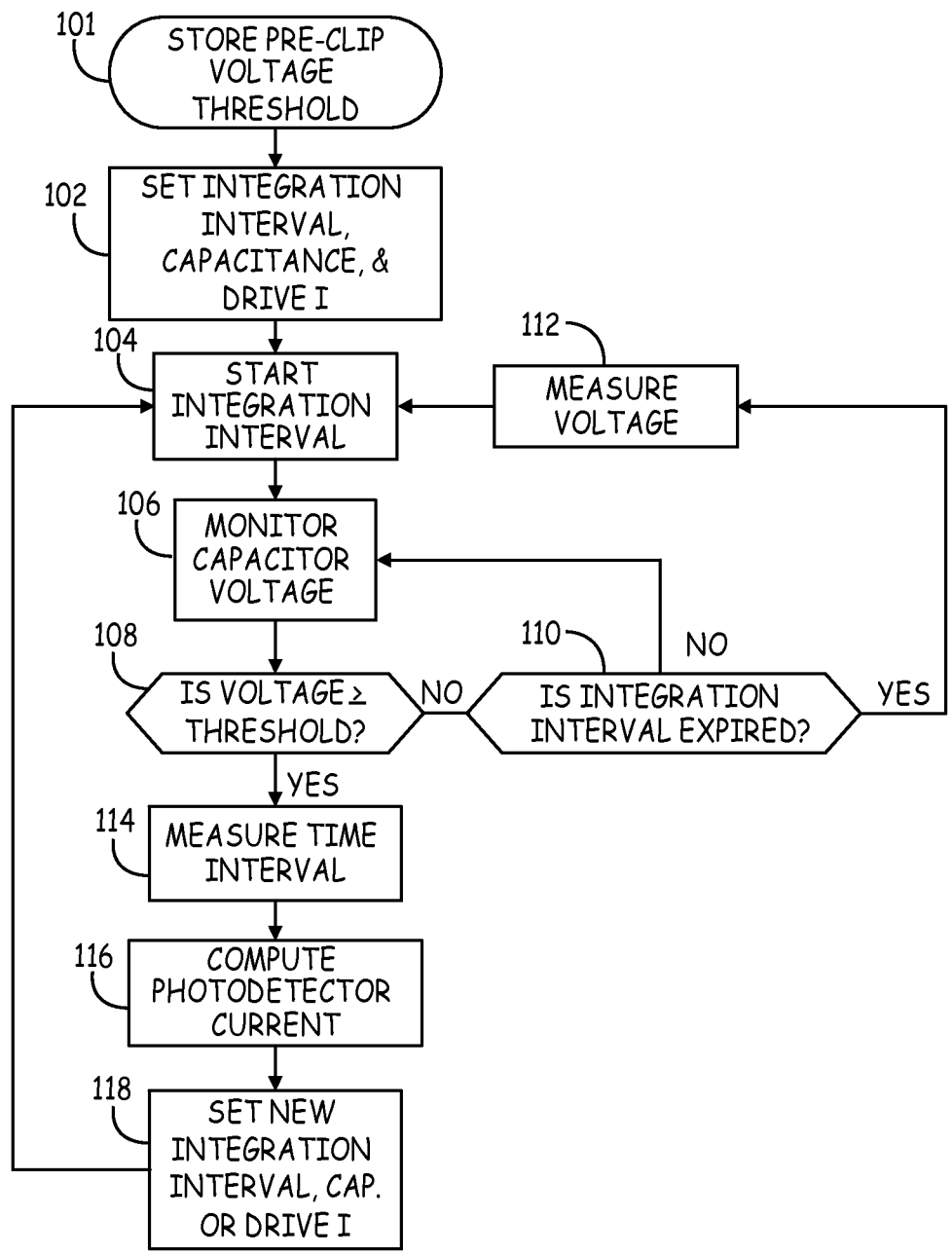
FIG. 5 is a flow chart of a method for operating an optical sensor for use in monitoring a physiological condition according to one embodiment.

FIG. 5 is a flow chart 100 of a method for operating an optical sensor for use in monitoring a physiological condition according to one embodiment. Flow chart 100, and other flow charts presented herein, are intended to illustrate the functional operation of the device, and should not be construed as reflective of a specific form of software, hardware or firmware necessary to practice the methods described. It is believed that the particular form of software or firmware will be determined primarily by the particular system architecture employed in the device and by the particular detection and therapy delivery methodologies employed by the device. Providing software, firmware, or hardware, or a combination thereof, to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 101, a pre-clip voltage threshold is stored. A pre-clip voltage threshold corresponds to a voltage just below the upper limit of an A/D converter input range. For example, if the upper limit of the A/D converter is approximately 1.2 V, the pre-clip threshold may be set to approximately 1.1 V.

At block 102, an initial integration time interval and integration capacitance used in an amplitude-based measurement as described above are set. Additionally, the drive current signal(s) applied to the optical sensor light source(s) are set. These three sensor control parameters will each affect the integrated capacitor voltage amplitude reached in response to the induced photodetector current. A long integration time interval, low integration capacitance, or high drive current (causing a high intensity of emitted light) can all lead to a relatively higher voltage amplitude and the potential for clipping. Furthermore, high ambient light conditions, particularly when the optical sensor is deployed to subcutaneous positions, or motion artifact, may cause signal clipping. Accordingly, each of the sensor control parameters listed above may be programmable and are automatically adjustable by the sensor drive circuit 80 and/or sensor processor and control circuit 82, also referred to herein as a "controller", for reducing the likelihood of signal clipping. The sensor operation control parameters of drive current, integration time interval, and integration capacitance are controlled, alone or in combination, to reduce the likelihood of the optical sensor voltage signal during an amplitude-based measurement method to exceed the upper limit of the A/D converter input range.

At block 104, an integration time interval is started during sensor operation according to a programmed monitoring protocol. During the integration interval, the optical sensor is emitting light which induces a photodetector current that is integrated over a capacitance. The integration capacitor voltage is monitored at block 106. In one embodiment, the integration capacitor voltage is provided as input to a comparator included in sensor processor circuit 82. The comparator compares the capacitor voltage to the pre-clip threshold at block 108.

If the capacitor voltage has not reached the pre-clip threshold, and the integration time interval has not expired as determined at decision block 110, the photodetector current continues to be integrated over the capacitance and the resulting voltage signal continues to be monitored at block 106. If the integration time interval does expire (affirmative result at block 110), without the capacitor voltage reaching the pre-clip threshold (negative result at block 108), the capacitor voltage provided as input to the A/D converter is measured as an optical signal sample point at block 112. The sampled measurement may be averaged with other samples or used directly in computing a measurement of a chromophore of interest in the adjacent tissue volume.

The process continues by returning to block 104 to start the next integration time interval in accordance with the monitoring protocol. To illustrate, the monitoring protocol may involve sampling photodetector current measurements several times per second, e.g. in the range of approximately 5 Hz to 60 Hz sampling, over a time interval of one second or more. This sampling may be repeated each minute, each hour, each day or according to a desired monitoring protocol, which will depend on the particular monitoring application and individual patient need. Sampling may also be initiated upon detecting a particular event which may arise from intrinsic cardiac electrical activity, heart sounds or other physiological sensed signal.

If the pre-clip threshold is reached or exceeded during an integration time interval as determined at decision block 108, the time expired in the integration time interval is measured at block 114. This measured time interval and the known integration capacitance can be used to adjust either integration time or integration capacitance to bring the signal back within the A/D converter input range. Alternatively, using the equation $i=C*dV/dt$, the photodetector current i is computed at block 116 and used in computing an adjusted sensor control parameter. In the foregoing equation, C is the known integration capacitance. The change in voltage (dV) is the pre-clip threshold less any offset of the integration capacitor. The change in time (dt) is the measured time interval when the pre-clip threshold was reached (or exceeded).

In one embodiment, the time interval will be measured at block 114 when the integration capacitance is equal to or greater than the pre-clip threshold at the next clock edge which increments the counter. At block 118, the integration capacitance is adjusted to bring the voltage signal back into the A/D converter range. Knowing the time to reach the pre-clip threshold and the integration capacitance, either the integration capacitance may be increased or the integration time may be shortened to avoid clipping.

For example, if integration capacitance is currently set at 2 pF, the integration time is currently set at 1 ms and the time to reach the preclip threshold voltage was 0.5 ms, the integration capacitance could be adjusted by the ratio of the programmed integration time to the pre-clip threshold time, e.g., (1 ms/0.5 ms)*2 pf=4 pf. Alternatively, the integration time may be set to a time interval shorter than the time to reach the preclip threshold, e.g. a time interval less than 0.5 ms.

Alternatively, when the photodetector current i is computed at block 116, a new capacitance C can be computed using the equation $i=C*dV/dt$, where dV equals a desired portion of the A/D converter range and dt equals the programmed integration time interval. For example, a desired or targeted voltage magnitude within the A/D converter range may be set to correspond to approximately two-thirds of the A/D converter range reserving the other one-third for ambient light fluctuation and motion artifact. Thus, dV in the above-described equation would be equal to two-thirds the A/D converter input range less any integration capacitor offset, dt equals the programmed integration time interval, and current i equals the computed photodetector current, leaving only C as an unknown to be solved for. By increasing the integration capacitance, the voltage signal may be brought back within the range of the A/D converter.

A targeted magnitude may be defined to include a tolerance range above and below the desired voltage magnitude. The portion of the A/D converter input range reserved for ambient light fluctuation and motion artifact may vary between embodiments and could be more or less than the one-third portion in the given example.

Alternatively, a computed photodetector current may be used to adjust the integration time interval at block 118. In this case, dt in the above equation is computed using the computed photodetector current i, the currently programmed integration capacitance C, and dV corresponding to a desired portion of the A/D converter range. By shortening the time interval, the voltage signal may be brought back to a desired magnitude within the A/D converter input range.

In still other embodiments, the drive current delivered to the light sources of the optical sensor may be adjusted at block 118 to bring the photodetector output signal back into the range of the A/D converter. In some embodiments, drive current applied to the light sources may be assumed to be proportional and substantially linear with the photodetector current. As such, if the photodetector current during a remitted light measurement is computed, a light source current may be adjusted to approximate the photodetector output current to be at a targeted range of the A/D converter, e.g. 50% of the input range. In particular, if the photodetector current during ambient light measurement alone is measured and the photodetector current during light emission by the optical sensor is measured, the portion of the photodetector current corresponding ambient light may be subtracted from the photodetector current during light emission to approximate photodetector current due to light emission. The light source current may then be set to a proportion of the photodetector current due to light emission.

After making the automatic adjustment to at least one of the integration capacitance, the integration time interval or the drive current activating the light source(s), the process returns to block 104 to start the next integration time interval. The time interval measured at block 114 at the pre-clip voltage is a time-based measurement corresponding to a fixed voltage amplitude (i.e. the pre-clip threshold). This time-based measurement provides information useful in computing adjusted settings applied at block 118 such that on the next integration time interval, the capacitor voltage will be back in the A/D converter range with a reduced likelihood of clipping. Thus, the method shown in flow chart 100 provides an amplitude-based optical sensor signal measurement system that utilizes time interval-based measurements to quickly restore in-range measurements when clipping occurs or is likely to occur. Such a system provides a high and predictable sampling rate possible with an amplitude-based measurement system while minimizing the likelihood of signal clipping and quickly restoring in-range measurements when clipping does occur.

By quickly adjusting the sensor signal voltage magnitude to be within the A/D converter range from one integration time interval to the next, a larger portion of the A/D converter range may be designated as the dynamic measurement range allowing for improved signal to noise ratio. If ambient light fluctuations or motion artifact cause the pre-clip threshold to be reached, the sensor system can be quickly adjusted using the measured time interval associated with the pre-clip voltage. This measurement allows a calculated adjustment to be made immediately instead of a more time-consuming binary search or other iterative method for adjusting a sensor control parameter until the voltage signal is within the A/D converter range.

Oftentimes, optical sensor signal measurements obtained over time are compared to each other to determine relative changes in the sensor output signal for indicating a change in a physiological condition. In such monitoring algorithms, adjustment of sensor control parameters during a sequence of measurements may make data analysis and interpretation difficult. Furthermore, in some embodiments, comparison of relative measurements must be made over relatively short time intervals to allow an IMD to quickly respond to a changing physiological condition by providing or adjusting a therapy.

For example, in the implementation shown in FIG. 3A, a subcutaneous optical sensor may be used to confirm ventricular fibrillation prior to defibrillation shock delivery. A determination of falling arterial blood oxygen saturation due to ventricular fibrillation may be made based on changes in relative blood oxygen saturation measurements performed over several seconds, for example less than 10 seconds.

Adjustment of optical sensor control parameters prior to a series of measurements that are to be compared allows direct comparison of measurements during a monitoring interval and more straight forward data interpretation. As long as the measurements performed over a monitoring interval do not cause A/D converter clipping, the measurements can be used to detect relative changes and a corresponding patient condition without further adjustment to the sensor control parameters during the monitoring interval. If a measurement clips, adjustments may become necessary and can be accomplished as described in the foregoing.

Figure 6:
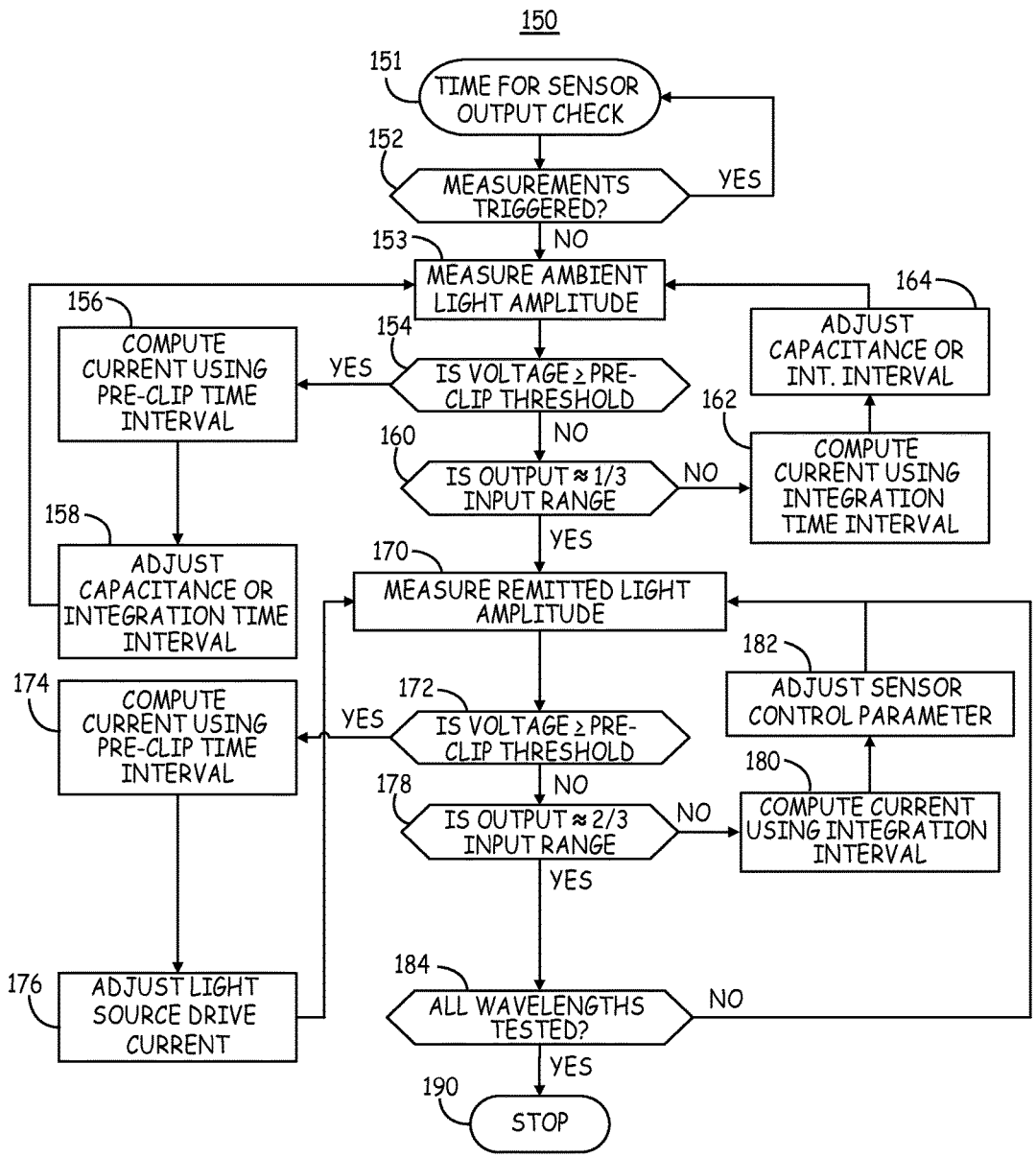
FIG. 6 is a flow chart of a method for adjusting optical sensor control parameters prior to a patient monitoring interval.

FIG. 6 is a flow chart 150 of a method for adjusting optical sensor control parameters prior to a patient monitoring interval. At block 151, the sensor controller determines if it is time to perform a check of the sensor output voltage for automatic adjustment of sensor control parameters. The method shown in FIG. 6 may be performed on a periodic basis, for example immediately preceding a programmed patient monitoring interval during which optical sensor signal measurements are obtained for use in monitoring or detecting a patient condition. The time for a sensor check may occur at a predetermined time interval prior to a programmed monitoring interval.

Generally, the sensor control parameter adjustment process may begin at block 151 at any time when the sensor is not being used for acquiring chromophore measurements. Sensor output signal checks may be scheduled to occur at regular time intervals. However when patient monitoring using the optical sensor is triggered by unpredictable events, such as the onset of ventricular fibrillation, a scheduled sensor output signal check may be delayed until triggered optical sensor signal measurements are completed. Alternatively, the sensor output check may be performed immediately upon triggering optical sensor signal measurements for patient monitoring purposes.

The sensor output signal check may be scheduled to occur as frequently as desired when the sensor is not being used for patient monitoring purposes so that, during actual patient monitoring intervals, the likelihood of having to adjust a sensor control parameter is reduced. In this way, a series of sampled signal measurements may be obtained using fixed sensor control parameters during a given monitoring interval in which relative changes of optical sensor measurements are used for detecting a patient condition. If at any time during the actual patient monitoring a pre-clip threshold is reached, however, adjustments may be needed and can be performed as described above in conjunction with FIG. 5.

Once the sensor output signal check is initiated, the ambient light amplitude is measured at block 153 using a programmed integration time interval. Ambient light is measured when the optical sensor light source(s) are not activated to emit light. If the voltage signal reaches a pre-clip threshold as detected at block 154, prior to the programmed integration time interval expiring, the time interval at which the pre-clip threshold was reached or exceeded is measured and used to either directly adjust the integration time interval or the integration capacitance at block 158 or to compute the photodetector current at block 156, which is then used to adjust a control parameter at block 158, as described previously. Direct adjustment of the integration time interval to an interval shorter than the measured pre-clip time interval or increasing the integration capacitance by a proportion determined using the ratio of the programmed integration time to the measured pre-clip time interval can be performed at block 158 in response to the measured time interval as described previously, without calculating the photodetector current.

Alternatively, a new integration capacitance or new integration time interval (or a combination of both) is computed at block 158 using the photodetector current computed at block 156 and the equation described above. The new control parameter is adjusted at block 158 to shift the ambient light signal to a desired target proportion of the A/D converter input range. For example, one-third of the A/D input range may be reserved for the ambient light signal and another one-third may be reserved to allow for fluctuation of the ambient light signal without clipping. This leaves one-third of the A/D converter input range for measurement of the reflected or transmitted light signal during light emission by the optical sensor. The adjusted capacitance or integration time interval at block 158 is computed using the measured pre-clip time interval. This adjustment may further involve computing a photodetector current at block 156 using the pre-clip time interval. The adjusted control parameter is then computed using the programmed integration capacitance or the programmed integration time interval, the photodetector current computed at block 156 and the targeted dV, which corresponds to one-third of the A/D converter input range (or other selected target range).

After adjusting the sensor control parameter at block 158, the process may return to block 153 to repeat the ambient light measurement to ensure that the ambient light signal falls in the targeted range using the newly adjusted sensor control parameter. Alternatively, the process may advance directly to block 170 to measure light when the optical sensor is emitting light.

If the ambient light signal does not reach the pre-clip threshold at block 154, the voltage amplitude at the end of the integration time interval is compared to the targeted proportion of the A/D converter input range, shown as approximately one-third of the A/D converter input range in this example at block 160. If the ambient light signal is outside of an acceptable targeted range (a negative result at decision block 160) the photodetector current is computed at block 162 using the programmed capacitance and integration time interval and the measured voltage at the expiration of the integration time interval. The computed current is used at block 164, using the equation $i=C*dV/dt$ to adjust either the capacitance or the integration time interval to shift the ambient light signal to fall within the targeted range.

The process then returns to block 153 to repeat the ambient light measurement using the adjusted sensor control parameter. Once the ambient light signal falls within the targeted range, the process advances to block 170. Alternatively, the process may advance directly from block 164 to block 170.

At block 170, a light source in the optical sensor is activated. The remitted light is measured at block 170 and includes both ambient light and light emitted by the sensor and reflected or transmitted to the light detecting portion of the sensor. The remitted light measurement is performed using the currently adjusted integration capacitance and integration time interval (based on the preceding ambient light measurements) and a previously programmed drive current signal applied to the light source.

During the integration time interval, the voltage signal is compared to a pre-clip threshold at block 172. If the voltage equals or exceeds the pre-clip threshold, the photodetector current is computed at block 174 using the time interval measured upon reaching or exceeding the pre-clip threshold as described previously. The computed photodetector current may be used to directly adjust the light source current at block 176 based on a known or assumed relation between the drive current and photodetector current.

For example, having just measured the ambient light using the same integration time and capacitance and knowing the ambient light signal has been adjusted within the target range, the light source current could be reduced by a proportion of the photodetector current to bring the voltage signal back within the A/D converter input range. The light source current may be assumed to be directly proportional and approximately linear with the photodetector current (minus the offset of the integration circuit and the photodetector current computed during the ambient light measurement). Knowing the current associated with the ambient light signal just measured and the total photodetector current allows the light source current to be adjusted to a proportion of the photodetector current that brings the photodetector current back into range. In other embodiments, a known non-linear relation between the light source current and the photodetector current may be used to adjust the light source current to bring the photodetector current back into a desired range.

Alternatively, the measured pre-clip time interval may be used directly or a photodetector current computed from the pre-clip time interval may be used to adjust the integration capacitance or the integration time interval instead of the light source current at block 176. After adjusting a sensor control parameter, the remitted light may be measured again at block 170 to verify that the sensor signal approaches the targeted proportion of the A/D converter input range.

If the sensor output signal does not reach or exceed the pre-clip threshold at block 172 during the integration time interval, the voltage amplitude at the expiration of the integration time interval is compared to a targeted proportion of the A/D converter input range at block 178. In this example, the output is compared to approximately two-thirds of the A/D converter range. In other words, the ambient light signal plus the light signal of interest is targeted to be approximately two-thirds of the A/D converter input range, reserving the remaining one-third for ambient light fluctuation and artifact.

If the output signal is not within the targeted range, the photodetector current is computed at block 180 using the programmed integration time interval, capacitance and measured voltage. The computed current and targeted signal range are then used to compute a new capacitance or integration time interval at block 182. A control parameter is adjusted to the computed value and the remitted light measurement may be repeated at block 170 to verify that the sensor signal is within the targeted range.

It is contemplated that a targeted range of the sensor output signal may vary between embodiments and a targeted signal range may depend on the magnitude of ambient light. For example, if ambient light is approximately 40% of the A/D converter input range, the sensor operating parameters may be adjusted to set the remitted light measurement at approximately 20% of the of the A/D converter input range. If the ambient light signal is low, e.g. approximately 10% of the input range, the sensor operating parameters may be adjusted to set the remitted light measurement (plus any integrator offset) at approximately 80% of the A/D converter input range. A minimum proportion of the A/D converter input range may be specified for reserving for ambient light fluctuation and artifact, e.g. 20%, 30% or other desired portion.

In this way, the sensor operating control parameters, i.e. the integration time interval, the integration capacitance, and the light source drive current, are adjusted, alone or in combination, to promote a high signal-to-noise ratio while reducing the likelihood of A/D converter clipping.

If more than one light source is included in the optical sensor, the process from block 172 through 184 may be repeated for additional light sources until all wavelength have been tested as determined at decision block 184. For example in a two-wavelength system including a red LED and an infrared LED, the red LED may be activated first at block 170 with parameters being adjusted until the sensor signal reaches the targeted range as determined at block 178. Then the red LED may be inactivated and the infrared LED activated and remitted light measurement is repeated at block 170 to allow any needed adjustments to bring the infrared light signal to a desired operating range.

When multiple wavelengths are being measured, only the light source drive current for the particular wavelength is adjusted to bring the remitted light signal to the desired operating point. Typically a single light detecting circuit operates using the same integration capacitance and integration time interval for measuring ambient light and all emitted light wavelengths. Therefore adjustments of capacitance or integration time interval will affect the output for all wavelengths being measured. Once integration capacitance and time interval are adjusted to set the ambient light signal at a targeted operating range, the capacitance and time interval remain fixed and only the light source current is adjusted to adjust any wavelength signals in the desired operating range. Alternatively, the capacitance or integration time interval may be adjusted for setting the ambient light signal and a first light wavelength within respective targeted operating ranges and any additional wavelength signals are adjusted using only the respective light source current.

If light source current adjustment alone does not achieve the desired result for additional wavelengths of emitted light, the ambient light intensity may have changed. It may be necessary to return to block 153 to re-adjust the integration time interval or capacitance to restore the ambient light signal back to the target range then proceed with adjusting the light source current for individual wavelengths as needed. In alternative embodiments, adjusting integration time and/or capacitance values independently for each wavelength may be performed.

After the signal range of all wavelengths (or light sources) has been tested with sensor control parameter adjustments made as needed, the sensor output check is stopped at block 190. It is understood that ambient light measurements may be repeated between testing of different emitted light wavelengths to ensure that ambient light is not changing significantly. It is also to be understood that the operations performed in flow chart 150 and other flow charts presented herein are not necessarily limited to the precise order shown and may be performed in another order, with some steps being optional, in other embodiments.

Figure 7:
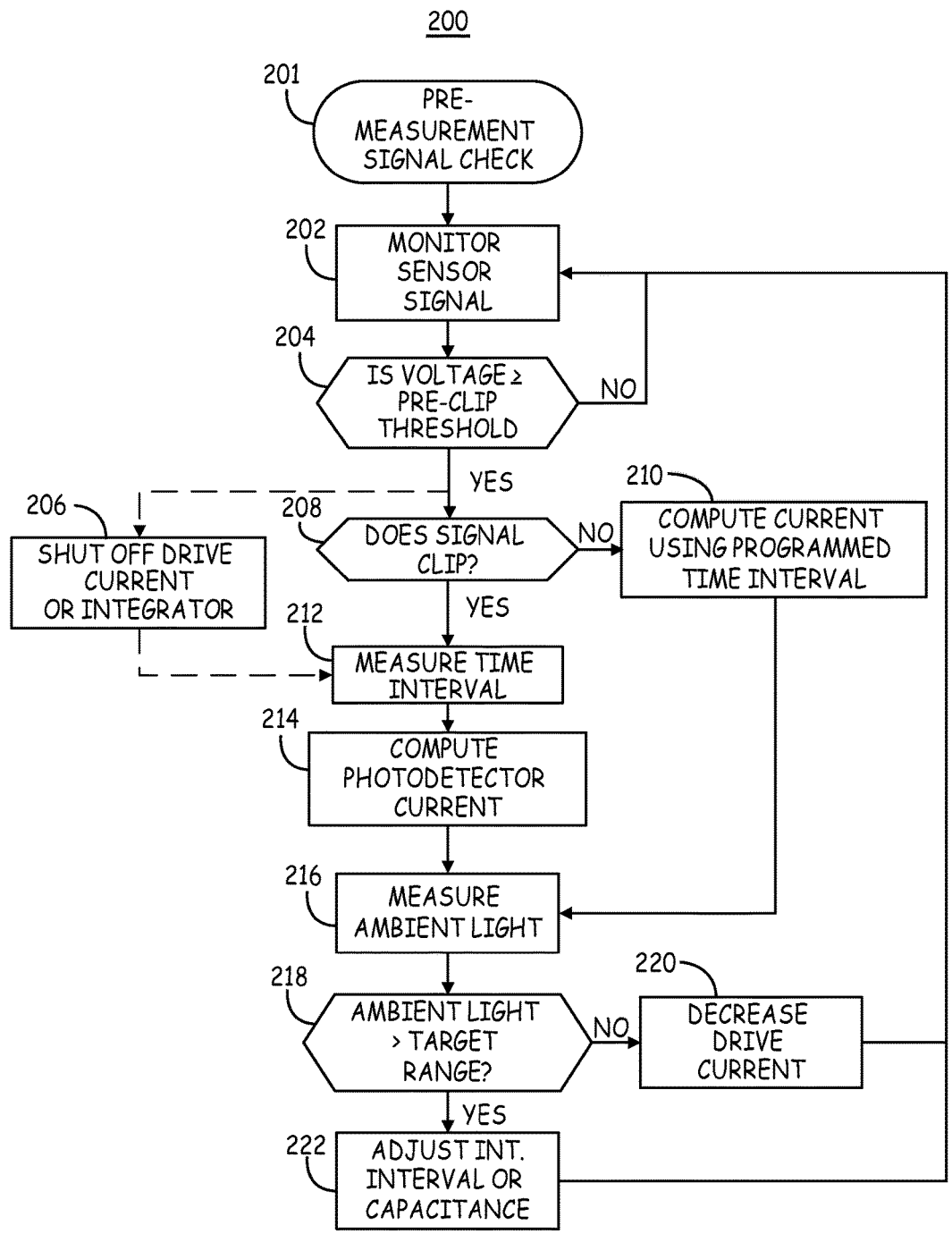
FIG. 7 is a flow chart of a method for operating an optical sensor according to an alternative embodiment.

FIG. 7 is a flow chart 200 of a method for monitoring an optical sensor signal according to an alternative embodiment. Prior to performing patient monitoring, a pre-measurement signal check may be performed at block 201 as described above in conjunction with FIG. 6. Adjustment of signal control parameters may be performed on a scheduled periodic basis or immediately prior to performing measurements, every time measurements are performed for detecting a patient condition or less frequently.

At block 202 optical sensor signal monitoring is performed according to a programmed monitoring protocol. The optical sensor signal is monitored to obtain a "packet" of measurements needed to compute an optical signal measurement. For example, in monitoring blood oxygen saturation, a "packet" may include an ambient light signal, a red light signal and an infrared light signal. Multiple "packets" may be sampled during a monitoring interval to enable computation of a monitored metric of the optical signal and comparison of the metric over a period of time. Ambient light measurements obtained during monitoring may be used for correcting red and infrared light measurements.

If the optical sensor signal remains within the A/D converter input range throughout the monitoring interval, it is not necessary to make any adjustment to sensor control parameters. During signal monitoring, the integration capacitor voltage is compared to a pre-clip threshold at block 204. As long as the capacitor voltage does not reach the pre-clip threshold, the sensor signal continues to be monitored using the current operating control parameters by returning to block 202.

If a signal reaches the pre-clip threshold, as determined at decision block 204, an adjustment may be made so that signal clipping can be avoided and the next packet of measurements will be in range of the A/D converter. Depending on the particular application, a threshold number of measurements reaching the pre-clip threshold (or actually clipping) may be tolerated before adjusting the sensor control parameters. For example, transient artifact that is very brief may cause signal clipping for one or more measurements but then the signal may return to the normal ND input range. Clipping of one or more measurements may be tolerated in some embodiments. In order to avoid frequent adjustments, a threshold number of times that the pre-clip threshold is reached may be applied prior to adjusting sensor control parameters.

In some embodiments, the threshold for making sensor control parameter adjustments may include a time-related criterion. For example, if the signal reaches the pre-clip threshold very near to the end of the integration time interval, adjustment of sensor control parameters may be delayed until the pre-clip threshold is reached a threshold number of times, earlier during the integration time interval, and/or actual clipping of the signal occurs. The criteria for making sensor control adjustments during patient monitoring may vary between embodiments and may depend on the time scale and urgency of the measurements being taken.

After detecting a pre-clip threshold signal at block 204, the time interval to reach the pre-clip threshold is measured at block 212 as generally described above. In the process shown by flow chart 200, the light source drive current may optionally be stopped or reduced or the integrator may be shut off at block 206 in response to reaching or exceeding the pre-clip threshold to prevent clipping. By taking one of these actions when the voltage has nearly reached a clipping voltage, clipping is prevented along with any undesirable effects of clipping on the sensor processor circuitry.

Alternatively, the integration time interval may be allowed to time out to determine if the signal actually does clip at block 208. If the signal does not actually clip, the currently programmed integration time interval and measured voltage at the end of the integration time interval can be used to compute the photodetector current at block 210. If the signal does clip, the time interval required to reach the pre-clip threshold (measured at block 212) and the pre-clip threshold voltage are used to compute the photodetector current at block 214. While not explicitly shown in FIG. 7, if the signal does not actually clip, the voltage signal at the expiration of the integration time interval may be used in determining an optical signal measurement. Additionally, knowledge of whether or not the signal actually clips may be used in deciding when and if sensor control parameters are adjusted to reduce the likelihood of clipping in future measurements.

After computing the photodetector current at either block 214 or block 210, a new capacitance or integration time interval may be computed directly and adjusted as described in conjunction with FIG. 5. Alternatively, the ambient light signal is measured at block 216 in response to a pre-clip threshold being reached. An increase in ambient light may be the cause of the clipped or nearly clipped signal. If the ambient light has increased, as determined at block 218, the integration time interval or capacitance is adjusted at block 222. A new integration time interval or capacitance is computed using the computed photodetector current and a targeted signal magnitude range. If ambient light has not increased above the target signal range for ambient light, the light source drive current for the signal that clipped or nearly clipped is adjusted at block 220. In this way, an ambient light measurement guides which sensor control parameter is adjusted based on whether an increase in ambient light was the cause of potential clipping.

If the ambient light signal has not increased as determined at decision block 218, the clipped or nearly clipped signal may be due to an increase in reflected or transmitted light. In this case, the drive signal current is adjusted at block 220 to reduce the emitted light intensity and thereby reduce the intensity of remitted light and return the signal to a desired magnitude in the A/D converter input range.

After adjusting a sensor control parameter at block 220 or block 222, the process returns to block 202 to continue monitoring the sensor signal. While not explicitly shown in FIG. 7, if a pre-clip threshold is reached at block 204 during an ambient light measurement during acquisition of a signal packet the process may advance directly to block 222 after computing the photodetector current at block 210 or 214. Likewise, if an ambient light signal measurement clips at block 216, the process may advance immediately to block 222. The integration interval and/or capacitance is adjusted at block 222. The pre-clip voltage and time interval at which the pre-clip threshold occurred are used to compute a photodetector current. Using the known photodetector current and a desired voltage change dV, the integration capacitance C or time interval dt to achieve a targeted voltage magnitude within the A/D converter range is computed as described above.

Thus, an apparatus and associated method for operating an optical sensor have been presented in the foregoing description with reference to specific embodiments. It is appreciated that various modifications to the referenced embodiments may be made without departing from the scope of the disclosure as set forth in the following claims.

The invention claimed is:

1. A method for measuring a signal produced by an optical sensor comprising a light source and a light detector, the method comprising:
   setting an integration time interval to an initial time interval programmed to obtain a voltage amplitude-based optical signal sample point;
   applying a drive current to activate the light source during the integration time interval;
   integrating a current induced on the light detector to obtain a voltage signal during the integration time interval, wherein the current is induced in response to a light transmitted from the light source to the light detector;
   comparing the voltage signal to a threshold during the integration time interval;
   converting the voltage signal to the optical signal sample point at the expiration of the integration time interval;
   adjusting an optical sensor control parameter in response to the voltage signal crossing the threshold during the integration time interval; and
   operating the optical sensor using the adjusted control parameter,
   wherein adjusting the optical sensor control parameter comprises:
      measuring a time interval for the voltage signal to reach the threshold during the integration time interval by measuring a duration of the integration time interval that has elapsed when the threshold is reached,
      computing a light detector current using the measured time interval, and
      computing the adjusted optical sensor control parameter using the computed light detector current.

2. The method of claim 1, further comprising:
   adjusting the optical sensor control parameter by adjusting the integration time interval to be shorter than the measured time interval in response to the voltage signal reaching the threshold during the integration time interval.

3. The method of claim 1, further comprising establishing the threshold below an input range maximum of an analog-to-digital converter receiving the voltage signal.

4. The method of claim 1, further comprising:
   establishing a targeted magnitude of the voltage signal as a proportion of an input range of an analog-to-digital converter receiving the voltage signal; and
   computing the adjusted control parameter to produce a voltage signal at the targeted magnitude upon expiration of the integration time interval.

5. The method of claim 4, further comprising:
   integrating the current signal for the integration time interval;
   comparing a voltage signal magnitude at an expiration of the integration time interval to the targeted magnitude when the voltage signal does not meet the threshold during the integration time interval; and
   adjusting an optical sensor control parameter in response to the signal magnitude falling outside the targeted magnitude.

6. The method of claim 1, further comprising turning off one of an integrator integrating the current and the drive current activating the light source in response to the voltage signal reaching the threshold.

7. The method of claim 1, further comprising:
   measuring ambient light in response to the voltage signal reaching the threshold;
   comparing the ambient light to a targeted ambient light signal range; and
   adjusting one of an integration time interval and an integration capacitance over which the voltage signal is obtained in response to the ambient light measurement exceeding the targeted range.

8. The method of claim 7, further comprising adjusting the drive current activating the light source in response to the ambient light measurement not exceeding the targeted range.

9. The method of claim 1, wherein adjusting an optical sensor control parameter comprises adjusting one of an integration capacitance, an integration time interval over which the current is integrated, and the drive current applied to the light source.

10. The method of claim 1, further comprising:
    adjusting the optical sensor control parameter to the computed optical sensor control parameter without iteratively adjusting the optical sensor control parameter so that a next optical signal sample point at an expiration of a next integration time interval immediately following the integration time interval is within a targeted range of the converter, the adjusted optical sensor control parameter comprising at least one of an increased integration capacitance of the light detector during the next integration time interval compared to during the initial integration time interval, a decreased duration of the next integration time interval compared to the initial integration time interval, and a decreased drive current during the next integration time interval compared to during the initial integration time interval.

11. A medical device for monitoring a patient using an optical sensor signal, the device comprising:

an optical sensor comprising a light source and a light detector;

a timer set to an initial integration time interval programmed to obtain a voltage amplitude-based optical signal sample point;

an integrator configured to integrate a current induced on the light detector to obtain a voltage signal, wherein the current is induced in response to a light transmitted from the light source to the light detector;

a converter configured to convert the voltage signal to the optical signal sample point at the expiration of the integration time interval;

a comparator configured to compare the voltage signal to a threshold during the integration time interval; and a controller configured to adjust an optical sensor control parameter in response to the voltage signal reaching the threshold during the integration time interval, and operate the optical sensor to produce the optical sensor signal using the adjusted control parameter, wherein adjusting the optical sensor control parameter comprises:

measuring a time interval for the voltage signal to reach the threshold during the integration time interval by measuring a duration of the integration time interval that has elapsed when the threshold is reached, computing a light detector current using the measured time interval, and computing the adjusted optical sensor control parameter using the computed light detector current.

12. The device of claim 11, wherein the controller is configured adjust the optical sensor control parameter in response to the voltage signal reaching the threshold during the integration time interval by adjusting the integration time interval to be shorter than the measured time interval.

13. The device of claim 11, further comprising an analog-to-digital converter to receive the voltage signal, wherein the threshold is below an input range maximum of the analog-to-digital converter.

14. The device of claim 11, further comprising an analog-to-digital converter receiving the voltage signal, wherein the controller is further configured to establish a targeted magnitude of the voltage signal as a proportion of an input range of the analog-to-digital converter and compute the adjusted control parameter to produce a voltage signal at the targeted magnitude upon expiration of the integration time interval.

15. The device of claim 14, wherein the integrator integrates the current signal for the integration time interval, the comparator compares a voltage signal magnitude upon expiration of the integration time interval to the targeted magnitude when the voltage signal does not meet the threshold during the integration time interval, and the controller adjusts an optical sensor control parameter in response to the voltage signal magnitude falling outside the targeted magnitude.

16. The device of claim 11, further comprising a drive circuit to deliver a drive current to the light source, the controller configured to turn off one of the integrator and the drive current activating the light source in response to the voltage signal reaching the threshold.

17. The device of claim 11, wherein the controller is further configured to measure ambient light in response to the voltage signal reaching the threshold, compare the ambient light to a targeted ambient light signal range, and adjust one of an integration time interval and an integration capacitance in response to the ambient light measurement exceeding the targeted range.

18. The device of claim 17, further comprising a drive circuit to deliver a drive current to the light source, the controller further configured to adjust the drive current in response to the ambient light measurement not exceeding the targeted range.

19. The device of claim 11, wherein adjusting an optical sensor control parameter comprises adjusting one of an integration capacitance, an integration time interval over which the current is integrated, and a drive current applied to the light source.

20. The device of claim 11, wherein the controller is configured to:

compute the light detector current using the equation $I1=C1*dV1/dt1$, where $dt1$ is the measured time interval, $dV1$ is the threshold voltage, $C1$ is an integration capacitance of the light detector, and $I1$ is the computed light detector current; and compute the adjusted optical sensor control parameter using the computed light detector current as one of an adjusted integration capacitance, an adjusted integration time interval and an adjusted drive current delivered to the light source.

21. The device of claim 20, wherein the adjusted optical sensor control parameter is computed as the adjusted integration capacitance using the equation $I1=C2*dV2/dt1$ where $C2$ is the adjusted integration capacitance and $dV2$ is a target magnitude of the voltage signal.

22. The device of claim 20, wherein the adjusted optical sensor control parameter is computed as the adjusted integration time interval using the equation $I1=C1*dV2/dt2$ where $dt2$ is the adjusted integration time interval and $dV2$ is a target magnitude of the voltage signal.

23. The device of claim 20, wherein the adjusted optical sensor control parameter is the drive current delivered to the light source computed as a proportion of the computed light detector current.

24. A medical device for monitoring a patient using an optical sensor signal, the device comprising:

an optical sensor comprising a light source and a light detector;

an integrator configured to integrate a current induced on the light detector to obtain a voltage signal;

a timer configured to set an initial integration time interval programmed to obtain a voltage amplitude-based optical signal sample point;

a converter configured to convert the voltage signal to the optical signal sample point at the expiration of the integration time interval;

a comparator configured to compare the voltage signal to a threshold during the integration time interval; and a controller configured to adjust an optical sensor control parameter in response to the voltage signal reaching the threshold during the integration time interval and operate the optical sensor to produce the optical sensor signal using the adjusted control parameter, wherein adjusting the optical sensor control parameter comprises:

measuring a first voltage signal when the optical sensor light source is not activated to emit light;

comparing the first voltage signal to a first threshold;

adjusting a first control parameter in response to the first voltage signal reaching the first threshold, the first control parameter adjusted to cause the first voltage signal to fall within a first target range;

initiating the integration time interval responsive to activation of the optical sensor light source;

measuring a second voltage signal during the integration time interval responsive to activating the optical sensor light source to emit light;

comparing the second voltage signal to a second threshold;

responsive to the second voltage signal reaching the second threshold during the integration time interval, measuring a duration of the integration time interval that has elapsed responsive to the second voltage signal reaching the threshold, computing a light detector current using the measured time interval, adjusting a second control parameter value using the computed light detector current to cause the second voltage signal to fall within a second target range, the second control parameter different than the first control parameter.

* * * * *

UNITED STATES PATENT AND TRADEMARK OFFICE
CERTIFICATE OF CORRECTION

PATENT NO. : 9,693,716 B2  
APPLICATION NO. : 13/044119  
DATED : July 4, 2017  
INVENTOR(S) : Robert Michael Ecker, Timothy J. Davis and James D. Reinke Page 1 of 1

It is certified that error appears in the above-identified patent and that said Letters Patent is hereby corrected as shown below:

In the Claims

Claim 20, Column 20, Line 31 delete "...capacitance of the light detector, and 11 is the computed..." and insert in place thereof -- "...capacitance of the light detector, and I1 is the computed..." --

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*